United States Patent
Bassler et al.

(10) Patent No.: US 7,550,064 B2
(45) Date of Patent: Jun. 23, 2009

(54) METHOD FOR CONTINUOUSLY OPERATED PURE DISTILLATION OF OXIRANES, ESPECIALLY PROPYLENE OXIDE

(75) Inventors: Peter Bassler, Viernheim (DE); Hans-Georg Goebbel, Kallstadt (DE); Joaquim Henrique Teles, Otterstadt (DE); Peter Rudolf, Ladenburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 711 days.

(21) Appl. No.: 10/517,368

(22) PCT Filed: Jul. 23, 2003

(86) PCT No.: PCT/EP03/08043

§ 371 (c)(1),
(2), (4) Date: Dec. 10, 2004

(87) PCT Pub. No.: WO2004/009204

PCT Pub. Date: Jan. 29, 2004

(65) Prior Publication Data

US 2005/0211541 A1    Sep. 29, 2005

(30) Foreign Application Priority Data

Jul. 23, 2002   (DE) ................................ 102 33 387

(51) Int. Cl.
*B01D 3/14* (2006.01)
*C07D 301/12* (2006.01)
*C07D 301/32* (2006.01)

(52) U.S. Cl. ................... 203/29; 203/99; 203/DIG. 19; 549/525; 549/541

(58) Field of Classification Search .............. 203/1–3, 203/29, 99, 100, DIG. 19; 549/525, 541
See application file for complete search history.

(56) References Cited

U.S. PATENT DOCUMENTS

| | | | |
|---|---|---|---|
| 2,471,134 A | 5/1949 | Wright | |
| 4,230,533 A | 10/1980 | Giroux | |
| 6,479,680 B1 * | 11/2002 | Bassler et al. | 549/529 |
| 6,958,111 B2 * | 10/2005 | Rust et al. | 202/158 |
| 7,084,310 B2 * | 8/2006 | Bassler et al. | 568/867 |
| 7,332,634 B2 * | 2/2008 | Bassler et al. | 568/868 |

FOREIGN PATENT DOCUMENTS

DE    196 23 609    12/1997

(Continued)

OTHER PUBLICATIONS

Gerd Kaibel, "Distillation columns with vertical partitions", Chem. Eng.Technol., vol. 10, pp. 92-98 1987.

(Continued)

*Primary Examiner*—Virginia Manoharan
(74) *Attorney, Agent, or Firm*—Oblon, Spivak, McClelland, Maier & Neustadt, P.C.

(57) ABSTRACT

The invention relates to a continuously operated process for the purification by distillation of the oxirane formed in the oxirane synthesis by reaction of a hydroperoxide with an organic compound, wherein the crude oxirane is separated in a dividing wall column into low-, intermediate- and high-boiling fractions and the oxirane is taken off as intermediate boiler at the side offtake in a concentration of at least 99.9%.

4 Claims, 4 Drawing Sheets

FOREIGN PATENT DOCUMENTS

| | | |
|---|---|---|
| DE | 197 23 949 | 12/1998 |
| EP | 122 367 | 10/1984 |
| EP | 0122367 * | 10/1984 |
| EP | 126 288 | 11/1984 |
| EP | 133 510 | 2/1985 |
| EP | 1 151 781 | 11/2001 |
| WO | 00/07965 | 2/2000 |
| WO | 02/40434 | 5/2002 |

OTHER PUBLICATIONS

Gerd Kaibel, et al., "Gestaltung destillativer trennungen unter einbeziehung thermodynamischer gesichtspunkte", Chem. Ing. Tech., vol. 61, No. 1, pp. 16-25 1989.

G. Kaibel, et al., Thermodynamics—guideline for the development of distillation column arrangements, Gas Separation and Purification, vol. 4, pp. 109-114 1990.

"Distillation's great leap foward?". Process Engineering, vol. 2, pp. 33-34 1993.

F. Lestak, et al., "Heat transfer across the wall of dividing wall columns", Trans ICHEME, vol. 72, part A, pp. 639-644 1994.

Figyes Lestak, et al., "Advanced distillation saves", Chemical Engineering, vol. 7, pp. 72-76 1997.

Ullmann's Encyclopedia of Industrial Chemistry, $5_{th}$ edition, vol. A13, pp. 447-456.

* cited by examiner

METHOD FOR CONTINUOUSLY OPERATED PURE DISTILLATION OF OXIRANES, ESPECIALLY PROPYLENE OXIDE

The present invention relates to a continuously operated process for the purification by distillation of the oxirane formed in the preferably coproduct-free oxirane synthesis by reaction of a hydroperoxide with an organic compound. The crude product obtained is separated in a dividing wall column into low-, intermediate- and high-boiling fractions and the oxirane is taken off as intermediate boiler at the side offtake of the column. In particular, the invention relates to the continuously operated purification by distillation of propylene oxide from the reaction of propylene with hydrogen peroxide.

In customary processes of the prior art, oxiranes can be prepared by reaction of suitable organic compounds with hydroperoxides in single-stage or multistage reactions.

Compared to a single-stage process, the excess of organic compound to be reacted can be kept relatively small in multistage processes. This increases the selectivity to oxirane formation.

For example, the multistage process described in WO 00/07965 provides for the reaction of the organic compound with a hydroperoxide to comprise at least the steps (i) to (iii):
  (i) reaction of the hydroperoxide with the organic compound to give a product mixture comprising the reacted organic compound and unreacted hydroperoxide,
  (ii) separation of the unreacted hydroperoxide from the mixture resulting from step (i),
  (iii) reaction of the hydroperoxide which has been separated off in step (ii) with the organic compound.

Accordingly, the reaction of the organic compound with the hydroperoxide takes place in at least two steps (i) and (iii), with the hydroperoxide separated off in step (ii) being reused in the reaction.

The reactions in steps (i) and (iii) are preferably carried out in two separate reactors, preferably fixed-bed reactors, with the reaction of step (i) preferably taking place in an isothermal reactor and the reaction of step (iii) taking place in an adiabatic reactor.

This process can be used generally for the reaction of alkenes with hydroperoxides to form oxiranes. The hydroperoxide used in this sequence is preferably hydrogen peroxide, and the organic compound is preferably brought into contact with a heterogeneous catalyst during the reaction.

Owing to the high selectivity of the reaction, this method of preparation is also referred to as coproduct-free oxirane synthesis.

In particular, the above process can be used for preparing propylene oxide from propylene and hydrogen peroxide. Here, the hydrogen peroxide conversion in step (i) is from about 85% to 90% and that in step (iii) is about 95% based on step (ii). Over both steps, a total hydrogen peroxide conversion of about 99% can be achieved at a propylene oxide selectivity of about 94-95%.

The crude oxirane obtained in this oxirane synthesis and the work-up still contains impurities. It is generally obtained in a concentration of about 95-99%. For it to be suitable as starting material for specific organic syntheses, e.g. in the preparation of polyurethanes, a higher concentration of at least 99.9% is frequently necessary. It therefore has to be subjected to a purification step.

The purification by distillation carried out according to the prior art is carried out in conventional columns with a side offtake or columns connected in series. This necessitates relatively complicated apparatus and a relatively high energy consumption, since the oxirane has to be distilled a number of times to achieve the abovementioned high purity.

It is an object of the present invention to optimize the purification by distillation of the oxiranes formed in the reaction of suitable organic compounds with hydroperoxides, in particular in terms of energy consumption and thermal stress. In particular, a process which is operated continuously and allows the oxiranes which have preferably been obtained by multistage reaction to be isolated in high purity by distillation with a small outlay in terms of apparatus and a low energy consumption is to be made available.

We have found that this object is achieved by use of a dividing wall column in a continuously operated process for the purification by distillation of the oxirane formed in the preferably coproduct-free oxirane synthesis by reaction of a hydroperoxide with an organic compound.

The present invention accordingly provides a continuously operated process for the purification by distillation of the oxirane formed in the oxirane synthesis by reaction of a hydroperoxide with an organic compound, wherein the crude oxirane is separated in a dividing wall column into low-, intermediate- and high-boiling fractions and the oxirane is taken off as intermediate boiler at the side offtake.

The oxirane can be obtained in a high purity of preferably at least 99.9% under mild distillation conditions by means of the process of the present invention. It can be separated off from impurities under low thermal stress, since only short residence times in the dividing wall column are necessary because of the single vaporization. This is highly advantageous for the distillation of the highly reactive and thermally labile oxiranes. For this reason, the novel process of the present invention leads to a reduced outlay in terms of apparatus and reduced energy consumption combined with improved product quality compared to the distillation processes disclosed in the prior art. This is highly advantageous for industrial use.

The process is preferably employed for the distillation of propylene oxide which is prepared by multistage reaction of propylene with hydrogen peroxide.

Distillation columns having side offtakes and a dividing wall, hereinafter also referred to dividing wall columns, are known. They represent a further development of distillation columns which have only the side offtake but no dividing wall. The use of the last-named conventional type of column is, however, restricted because the products taken off at the side offtakes are never completely pure. In the case of products taken off at the side offtakes in the reinforcement section of the column, which are usually taken off in liquid form, the side product still contains proportions of low-boiling components which should be separated off via the top. In the case of products taken off at side offtakes in the stripping section of the column, which are usually taken off in gaseous form, the side product still contains proportions of high boilers. The use of conventional side offtake columns is therefore restricted to cases in which contaminated side products are permissible.

When a dividing wall is installed in such a column, the separation action can be improved and it becomes possible for side products to be taken off in pure form. A dividing wall is installed in the middle region above and below the feed point and the side offtake. This can be fixed in place by welding or can be merely pushed into place. It seals off the offtake section from the inflow section and prevents crossmixing of liquid and vapor streams over the entire column cross section in this part of the column. This reduces the total number of distillation columns required in the fractionation of multicomponent mixtures whose components have similar boiling points.

This type of column has been used, for example, for the separation of an initial mixture of the components methane, ethane, propane and butane (U.S. Pat. No. 2,471,134), for the separation of a mixture of benzene, toluene and xylene (U.S. Pat. No. 4,230,533) and for the separation of a mixture of n-hexane, n-heptane and n-octane (EP 0 122 367).

Dividing wall columns can also be used successfully for separating mixtures which boil azeotropically (EP 0 133 510).

Finally, dividing wall columns in which chemical reactions can be carried out with simultaneous distillation of the products are also known. Examples which may be mentioned are esterifications, transesterifications, saponifications and acetalizations (EP 0 126 288).

BRIEF DESCRIPTION OF THE DRAWINGS

FIG. 1 schematically shows the purification of the oxirane formed in the oxirane synthesis by distillation in a dividing wall column. Here, the crude oxirane from the oxirane synthesis is introduced as feed Z into the column. In the column, this crude oxirane is separated into a fraction comprising the low boilers L, for example, decomposition and dissociation products such as acetaldehyde and methyl formate, and a high-boiling fraction S which comprises, for example, solvent and water. The high-purity oxirane is taken off at the side offtake for intermediate boilers M.

Figure 1:
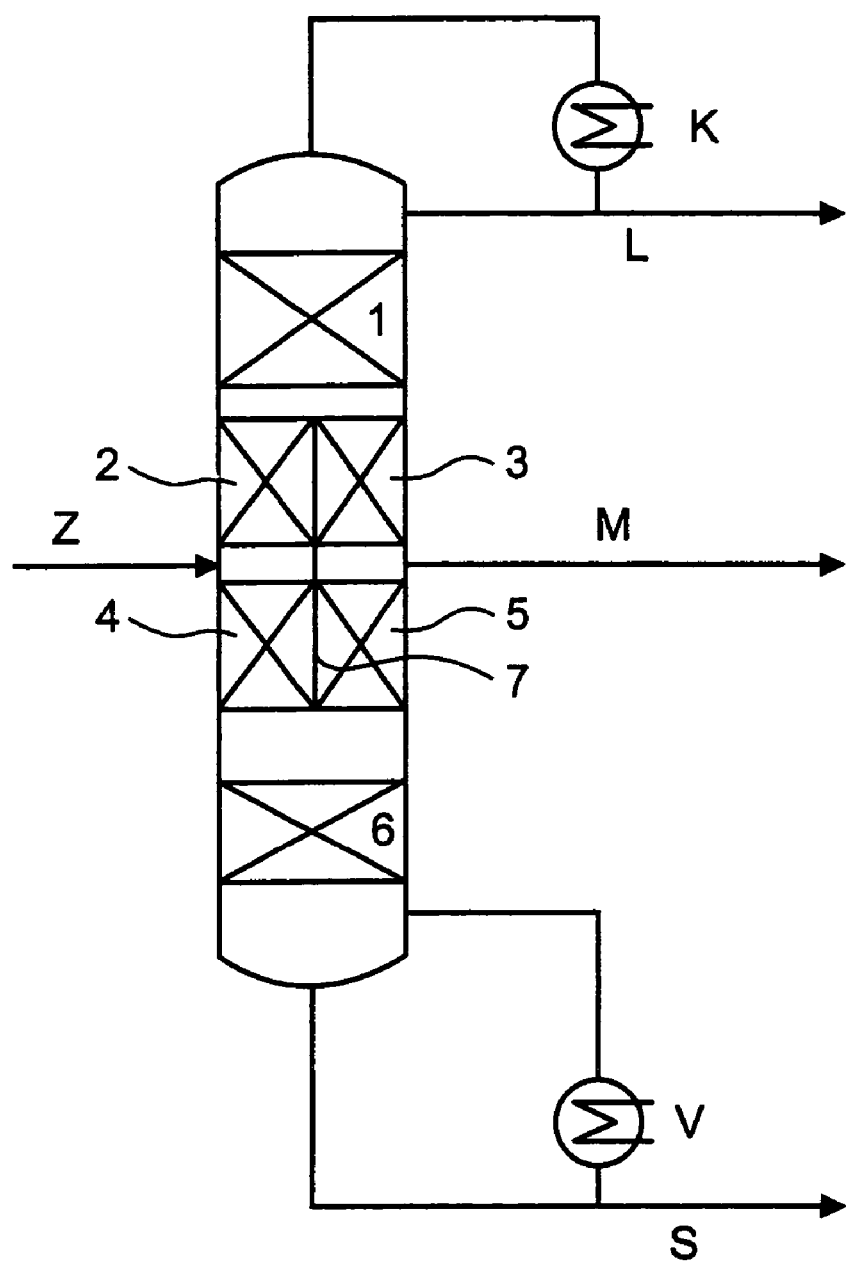
FIG. 1 shows purification of an oxirane by distillation in a dividing wall column.

To take off the product at the side offtake, it is possible to use receivers in which the liquid or condensing vapor can be collected and which may be located either inside or outside the column.

The process described in WO 00/07965 and the apparatus for carrying out this process are preferably used for the oxirane synthesis. The apparatus consists of an isothermal fixed-bed reactor, a separation apparatus and an adiabatic fixed-bed reactor.

Accordingly, the process of the present invention is suitable for the preferably continuous purification by distillation of an oxirane which is prepared by a process comprising at least the steps (i) to (iii) as defined above.

To carry out the process of the present invention, it is possible to use customary dividing wall columns having one or two side offtakes, for instance the columns described in the prior art.

Such a dividing wall column preferably has from 30 to 120, more preferably from 45 to 100, theoretical plates. The process of the present invention can be carried out particularly advantageously using such a design.

The upper combined region 1 of the inflow and offtake part of the dividing wall column preferably has from 5 to 50%, more preferably from 15 to 30%, of the total number of theoretical plates in the column, the enrichment section 2 of the inflow part preferably has from 5 to 50%, more preferably from 15 to 30%, the stripping section 4 of the inflow part preferably has from 5 to 50%, more preferably from 15 to 30%, the stripping section 3 of the offtake part preferably has from 5 to 50%, more preferably from 15 to 30%, the enrichment section 5 of the offtake part preferably has from 5 to 50%, more preferably from 15 to 30%, and the lower combined region 6 of the inflow and offtake part of the column preferably has from 5 to 50%, more preferably from 15 to 30%, in each case of the total number of theoretical plates in the column.

The sum of the number of theoretical plates in the regions 2 and 4 in the inflow part is preferably from 80 to 110%, more preferably from 90 to 100%, of the sum of the number of theoretical plates in the regions 3 and 5 in the offtake part.

It is likewise advantageous for the inlet via which the feed Z is fed into the column and the side offtake via which the oxirane is taken off as intermediate boiler to be arranged at different heights in the column relative to the position of the theoretical plates. The inlet is preferably located at a position which is from 1 to 8, more preferably from 3 to 5, theoretical plates above or below the side offtake.

The dividing wall column used in the process of the present invention is preferably configured either as a packed column containing random packing or ordered packing or as a tray column. For example, it is possible to use sheet metal or mesh packing having a specific surface area of from 100 to 1000 $m^2/m^3$, preferably from about 250 to 750 $m^2/m^3$, as ordered packing. Such packing provides a high separation efficiency combined with a low pressure drop per theoretical plate.

In the abovementioned configuration of the column, the region of the column divided by the dividing wall, which consists of the enrichment section 2 of the inflow part, the stripping section 3 of the offtake part, the stripping section 4 of the inflow part and the enrichment section 5, or parts thereof is/are provided with ordered packing or random packing. The dividing wall can be thermally insulated in these regions.

The crude oxirane is then introduced continuously into the column in the form of the feed stream Z which comprises components having boiling points lower and higher than the oxirane. This feedstream is generally liquid. However, it can be advantageous to subject the feedstream to preliminary vaporization and subsequently introduce it into the column as a two-phase, i.e. gaseous and liquid, mixture or in the form of one gaseous stream and one liquid stream. This preliminary vaporization is particularly useful when the feedstream contains relatively large amounts of low boilers. The preliminary vaporization enables a considerable load to be taken off the stripping section of the column.

The feedstream is advantageously metered by means of a pump or via a static inflow head of at least 1 m into the inflow part. This inflow is preferably regulated via a cascade regulation in combination with the regulation of the liquid level in the inflow part. The regulation is set so that the amount of liquid introduced into the enrichment section 2 cannot drop below 30% of the normal value. It has been found that such a procedure is important to even out troublesome fluctuations in the amount or concentration of the feed.

It is likewise important for the division of the liquid flowing down from the stripping section 3 of the offtake part of the column between the side offtake and the enrichment section 5 of the offtake part is set by means of a regulation device so that the amount of liquid going to the region 5 cannot drop below 30% of the normal value.

Adherence to these prerequisites has to be ensured by means of appropriate regulation methods.

Regulation mechanisms for the operation of dividing wall columns have been described, for example, in Chem. Eng. Technol. 10 (1987) 92-98, Chem.-Ing.-Technol. 61 (1989), No. 1, 16-25, Gas Separation and Purification 4 (1990) 109-114, Process Engineering 2 (1993) 33-34, Trans IChemE 72 (1994) Part A 639-644, Chemical Engineering 7 (1997)

72-76. The regulation mechanisms described in this prior art can also be employed for or applied to the process of the present invention.

The regulation principle described below has been found to be particularly useful for the continuously operated purification of the oxirane by distillation. It is readily able to cope with fluctuations in loading. The distillate is thus preferably taken off under temperature control.

A temperature regulation device which utilizes the downflow quantity, the reflux ratio or preferably the quantity of runback as regulating parameter is provided in the upper section 1 of the column. The measurement point for the temperature regulation is preferably located from 3 to 8, more preferably from 4 to 6, theoretical plates below the upper end of the column.

Appropriate setting of the temperature then results in the liquid flowing down from the section 1 of the column being divided at the upper end of the dividing wall so that the ratio of the liquid flowing to the inflow part to that flowing to the offtake part is preferably from 0.1 to 1.0, more preferably from 0.3 to 0.6.

In this method, the downflowing liquid is preferably collected in a receiver which is located in or outside the column and from which the liquid is then fed continuously into the column. This receiver can thus take on the task of a pump reservoir or provide a sufficiently high static head of liquid which makes it possible for the liquid to be passed on further in a regulated manner by means of regulating devices, for example valves. When packed columns are used, the liquid is firstly collected in collectors and from there conveyed to an internal or external receiver.

The vapor stream at the lower end of the dividing wall 7 is set by selection and/or dimensioning of the separation internals and/or incorporation of pressure-reducing devices, for example orifice plates, so that the ratio of the vapor stream in the inflow part to that in the offtake part is preferably from 0.8 to 1.2, preferably from 0.9 to 1.1.

In the abovementioned regulation principle, a temperature regulation device which utilizes the quantity taken off at the bottom as regulating parameter is provided in the lower combined section 6 of the column. The bottom product can therefore be taken off under temperature control. The measurement point for the temperature regulation device is preferably located from 3 to 6, more preferably from 4 to 6, theoretical plates above the lower end of the column.

In addition, the level regulation in column section 6 and thus for the bottom of the column can be utilized for regulating the quantity taken off at the side offtake. For this purpose, the liquid level in the vaporizer is used as regulating parameter.

The differential pressure over the column can also be utilized as regulating parameter for the heating power. The distillation is advantageously carried out at a pressure at the top of from 1 to 10 bar, preferably from 2 to 5 bar. Accordingly, the heating power of the vaporizer at the bottom of the column is selected to maintain this pressure range.

The distillation is then preferably carried out in a temperature range from 35 to 110° C., more preferably from 45 to 90° C. The distillation temperature is measured at the side offtake.

In the case of the distillation of crude propylene oxide, a pressure of about 3 bar and a temperature at the side offtake of about 60° C. have been found to be particularly useful and allow a high-purity propylene oxide to be obtained.

To be able to operate the dividing wall column in a trouble-free manner, the abovementioned regulation mechanisms are usually employed in combination.

In the separation of multicomponent mixtures into low-boiling, intermediate-boiling and high-boiling fractions, there are usually specifications in respect of the maximum permissible proportion of low boilers and high boilers in the middle fraction. Here, individual components which are critical to the separation problem, referred to as key components, or else the sum of a plurality of key components are/is specified.

Adherence to the specification for the high boilers in the intermediate-boiling fraction is preferably regulated via the division ratio of the liquid at the upper end of the dividing wall. The division ratio is set so that the concentration of key components for the high-boiling fraction in the liquid at the upper end of the dividing wall amounts to from 10 to 80% by weight, preferably from 30 to 50% by weight, of the value which is to be achieved in the stream taken off at the side. The liquid division can then be set so that when the concentration of key components of the high-boiling fraction is higher, more liquid is introduced into the inflow section, and when the concentration of key components is lower, less liquid is introduced into the inflow section.

Accordingly, the specification for the low boilers in the intermediate-boiling fraction is regulated by means of the heating power. Here, the heating power in the vaporizer is set so that the concentration of key components for the low-boiling fraction in the liquid at the lower end of the dividing wall amounts to from 10 to 80% by weight, preferably from 30 to 50% by weight, of the value which is to be achieved in the product taken off at the side. Thus, the heating power is set so that when the concentration of key components of the low-boiling fraction is higher, the heating power is increased, and when the concentration of key components of the low-boiling fraction is lower, the heating power is reduced.

The concentration of low and high boilers in the intermediate-boiling fraction can be determined by customary analytical methods. For example, infrared spectroscopy can be used for detection, with the compounds present in the reaction mixture being identified by means of their characteristic absorptions. These measurements can be carried out in-line directly in the column. However, preference is given to using gas-chromatographic methods. In this case, sampling facilities are then provided at the upper and lower end of the dividing wall. Liquid or gaseous samples can then be taken continuously or at intervals from the column and analyzed to determine their compositions. The appropriate regulation mechanisms can then be activated as a function of the composition.

In a specific embodiment of the dividing wall column, it is also possible for the inflow part and offtake part which are separated from one another by the dividing wall 7 not to be present in one column but to be physically separate from one another. In this specific embodiment, the dividing wall column can thus comprise at least two physically separate columns which then have to be thermally coupled with one another. Such thermally coupled columns exchange vapor and liquid between them, but energy is introduced via only one column. This specific embodiment has the advantage that the thermally coupled columns can also be operated under different pressures, which can make it possible to achieve better setting of the temperature level required for the distillation than in the case of a conventional dividing wall column.

Figure 2:
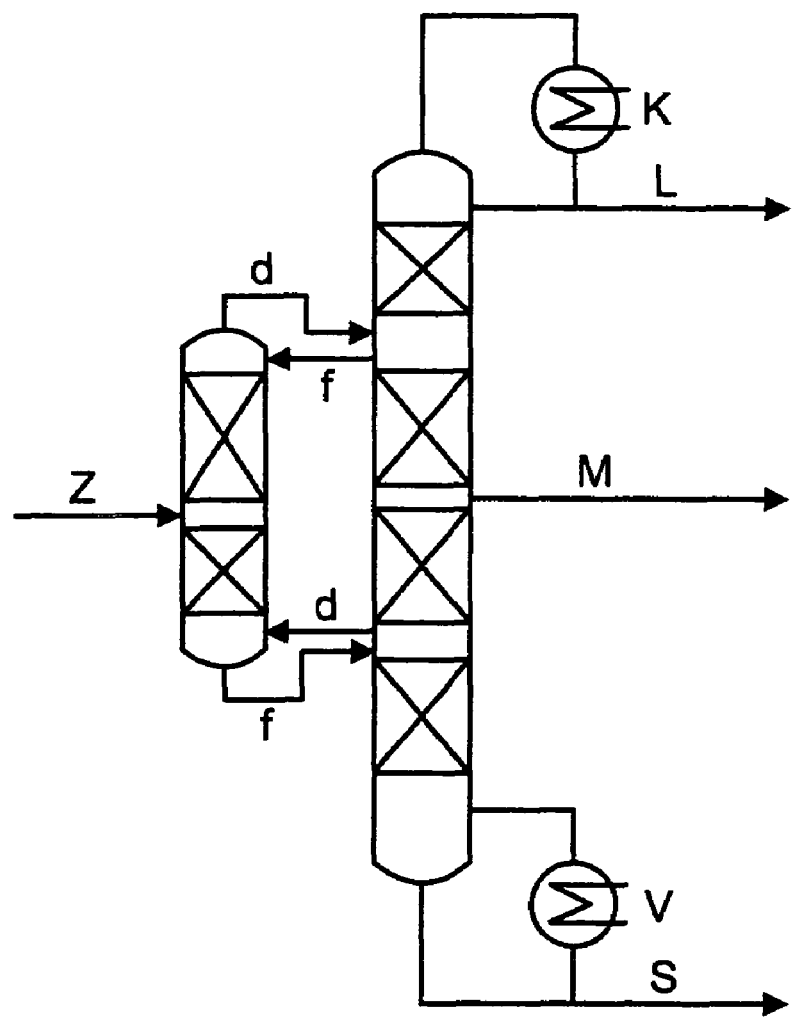
FIG. 2 shows purification of an oxirane by distillation using two dividing wall columns.
Figure 3:
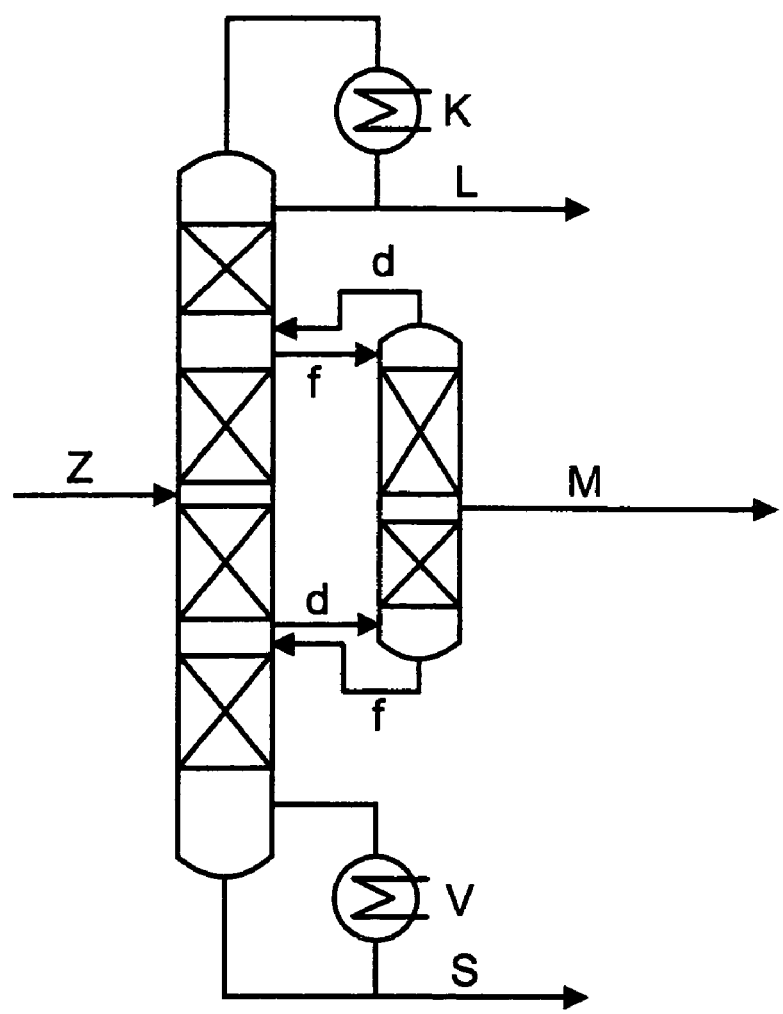
FIG. 3 shows purification of an oxirane by distillation using two dividing wall columns.

Examples of dividing wall columns in the specific embodiment of thermally coupled columns are shown schematically in FIGS. 2 and 3.

FIG. 2 shows a variant in which energy is introduced via the vaporizer V of the column which is located downstream of the column provided with the inlet for the feed Z, viz. the crude oxirane. In this arrangement, the crude oxirane is firstly separated into a low-boiling fraction and a high-boiling fraction, each of which also contain intermediate boilers, in the first column. The resulting fractions are subsequently transferred to the second column, with the low-boiling fraction comprising intermediate boilers being fed in at the upper end of the second column and the high-boiling fraction comprising intermediate boilers being fed in at the lower end. The low boilers L are distilled off via the top of the column and condensed via the condenser K. The high boilers S are obtained in the bottoms from the column. The high-purity propylene oxide can be taken off at the side offtake for intermediate boilers M. The two columns can exchange vapor and liquid via d and f.

FIG. 3 shows a further variant of thermally coupled columns. In this embodiment, the energy is introduced via the vaporizer V of the column into which the crude oxirane is also fed as feed Z. The low boilers L are distilled off via the top of this column and are condensed by means of the condenser K. The high boilers S are obtained in the bottoms. Low boilers L enriched with intermediate boilers are then transferred to the upper part of the downstream column and high boilers S enriched with intermediate boilers are transferred to the lower part of the downstream column. The high-purity propylene oxide can be taken off from the side offtake for intermediate boilers M. The two columns can exchange vapor and liquid via d and f.

The columns of FIGS. 2 and 3 can also be configured as packed columns containing random packing or ordered packing or as tray columns. For example, sheet metal or mesh packing having a specific surface area of from 100 to 1000 $m^2/m^3$, preferably from about 250 to 750 $m^2/m^3$, can be used as ordered packing. Such packing provides a high separation efficiency combined with a low pressure drop per theoretical plate.

An objective of the process of the present invention is to obtain oxiranes in which no impurity is present in a concentration of above 0.1% or in which the sum of all impurities is not greater than 0.1%. In particular, oxiranes having a purity of preferably at least 99.9%, but particularly preferably at least 99.99%, should be obtained. The percentages quoted are by weight, with the sum of oxirane and further components present therein being 100%.

If the process of the present invention is employed for purifying propylene oxide by distillation, the propylene oxide should be obtained in a purity of preferably at least 99.99% by weight. The concentration of key components of the low boilers (e.g. acetaldehyde, methyl formate) and of key components of the high boilers (e.g. methanol, water, propylene glycol) in the product should preferably be less than 0.01% by weight, based on a total of 100% by weight.

To obtain the oxirane to be purified by continuously operated distillation in a dividing wall column in the process of the present invention, it is possible to use the starting materials known from the prior art for the preferably coproduct-free oxirane synthesis.

Preference is given to using organic compounds which have at least one C—C double bond. Examples of such organic compounds having at least one C—C double bond include the following alkenes:

ethene, propylene, 1-butene, 2-butene, isobutene, butadiene, pentenes, piperylene, hexenes, hexadienes, heptenes, octenes, diisobutene, trimethylpentene, nonenes, dodecene, tridecene, tetradecene to eicosene, tripropene and tetrapropene, polybutadienes, polyisobutenes, isoprene, terpenes, geraniol, linalool, linalyl acetate, methylenecyclopropane, cyclopentene, cyclohexene, norbornene, cycloheptene, vinylcyclohexane, vinyloxirane, vinylcyclohexene, styrene, cyclooctene, cyclooctadiene, vinylnorbornene, indene, tetrahydroindene, methylstyrene, dicyclopentadiene, divinylbenzene, cyclododecene, cyclododecatriene, stilbene, diphenylbutadiene, vitamin A, beta-carotene, vinylidene fluoride, allyl halides, crotyl chloride, methallyl chloride, dichlorobutene, allyl alcohol, methallyl alcohol, butenols, butenediols, cyclopentenediols, pentenols, octadienols, tridecenols, unsaturated steroids, ethoxyethene, isoeugenol, anethole, unsaturated carboxylic acids such as acrylic acid, methacrylic acid, crotonic acid, maleic acid, vinylacetic acid, unsaturated fatty acids such as oleic acid, linoleic acid, palmitic acid, naturally occurring fats and oils.

Preference is given to alkenes having from 2 to 8 carbon atoms. Particular preference is given to reacting ethene, propene and butene. Very particular preference is given to reacting propene.

As hydroperoxide, it is possible to use the known hydroperoxides which are suitable for the reaction with the organic compound. Examples of such hydroperoxides are tert-butyl hydroperoxide and ethylbenzene hydroperoxide. Preference is given to using hydrogen peroxide as hydroperoxide for the oxirane synthesis, with an aqueous hydrogen peroxide solution also being able to be used.

The preparation of hydrogen peroxide can be carried out using, for example, the anthraquinone process by means of which virtually the entire world production of hydrogen peroxide is produced. This process is based on the catalytic hydrogenation of an anthraquinone compound to form the corresponding anthrahydroquinone compound, subsequent reaction of this with oxygen to form hydrogen peroxide and subsequent extraction to separate off the hydrogen peroxide formed. The catalysis cycle is closed by renewed hydrogenation of the anthraquinone compound which is obtained back.

An overview of the anthraquinone process is given in "Ullmann's Encyclopedia of Industrial Chemistry", $5^{th}$ Edition, Volume 13, pages 447 to 456.

It is likewise conceivable to obtain hydrogen peroxide by converting sulfuric acid into peroxodisulfuric acid by anodic oxidation with simultaneous evolution of hydrogen at the cathode. Hydrolysis of the peroxodisulfuric acid then leads via peroxomonosulfuric acid to hydrogen peroxide and sulfuric acid, which is thus recovered.

It is of course also possible to prepare hydrogen peroxide from the elements.

In the synthesis of the oxirane from the hydroperoxide and the organic compound, one or more suitable catalysts can be added to increase the efficiency of the reaction. Here, heterogeneous catalysts are preferably used.

All heterogeneous catalysts which are suitable for the respective reaction are conceivable. Preference is given to using catalysts which comprise a porous oxidic material, e.g. a zeolite. The catalysts used preferably comprise a titanium-, germanium-, tellurium-, vanadium-, chromium-, niobium- or zirconium-containing zeolite as porous oxidic material.

Specific mention may be made of titanium-, germanium-, tellurium-, vanadium-, chromium-, niobium- and zirconium-containing zeolites having a pentasil zeolite structure, in particular the types which can be assigned X-ray-crystallographically to the ABW, ACO, AEI, AEL, AEN, AET, AFG, AFI, AFN, AFO, AFR, AFS, AFI, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WIE, WEN, YUG, ZON structure or to mixed structures comprising two or more of the above-mentioned structures. Furthermore, titanium-containing zeolites having the ITQ-4, SSZ-24, TTM-1, UTD-1, CIT-1 or CIT-5 structure are also conceivable for use in the process of the present invention. Further titanium-containing zeolites which may be mentioned are those of the ZSM-48 or ZSM-12 structure.

Particular preference is given to Ti zeolites having an MFI or MEL structure or an MFI/MEL mixed structure. Very particular preference is given to the titanium-containing zeolite catalysts which are generally referred to as "TS-1", "TS-2", "TS-3" and also Ti zeolites having a framework structure isomorphous with β-zeolite.

In particular, it is advantageous to use a heterogeneous catalyst comprising the titanium-containing silicalite TS-1.

It is possible to use the porous oxidic material as such as catalyst. However, it is of course also possible for the catalyst used to be a shaped body comprising the porous oxidic material. All processes known from the prior art can be used for producing the shaped body from the porous oxidic material.

Noble metals in the form of suitable noble metal components, for example in the form of water-soluble salts, can be applied to the catalyst material before, during or after the one or more shaping steps in these processes. This method is preferably employed for producing oxidation catalysts based on titanium silicates or vanadium silicates having a zeolite structure, and it is thus possible to obtain catalysts which contain from 0.01 to 30% by weight of one or more noble metals from the group consisting of ruthenium, rhodium, palladium, osmium, iridium, platinum, rhenium, gold and silver. Such catalysts are described, for example, in DE-A 196 23 609.6.

Of course, the shaped bodies can be processed further. All methods of comminution are conceivable, for example splitting or crushing the shaped bodies, as are further chemical treatments as are described above by way of example.

When a shaped body or a plurality thereof is used as catalyst, it/they can, after deactivation has occurred in the process of the present invention, be regenerated by a method in which the deposits responsible for deactivation are burned off in a targeted manner. This is preferably carried out in an inert gas atmosphere containing precisely defined amounts of oxygen-donating substances. This regeneration process is described in DE-A 197 23 949.8. It is also possible to use the regeneration processes mentioned there in the discussion of the prior art.

As solvents, it is possible to use all solvents which completely or at least partly dissolve the starting materials used in the oxirane synthesis. Examples of solvents are aliphatic, cycloaliphatic and aromatic hydrocarbons, esters, ethers, amides, sulfoxides and ketones and also alcohols. The solvents can also be used in the form of mixtures. Preference is given to using alcohols. The use of methanol as solvent is particularly preferred.

As reactors for the oxirane synthesis, it is of course possible to use all conceivable reactors which are best suited to the respective reactions. A reactor is not restricted to an individual vessel for the oxirane synthesis. Rather, it is also possible to use, for example, a cascade of stirred vessels.

Fixed-bed reactors are preferably used as reactors for the oxirane synthesis. Further preference is given to using fixed-bed tube reactors as fixed-bed reactors.

In the above-described oxirane synthesis which is preferably employed, particular preference is given to using an isothermal fixed-bed reactor as reactor for step (i) and an adiabatic fixed-bed reactor for step (iii).

It is also possible to react a plurality of organic compounds with the hydroperoxide. It is likewise conceivable to use a plurality of hydroperoxides for the reaction. If, for example, two organic compounds and/or a plurality of hydroperoxides are reacted with one another in the respective steps, various products resulting from the reactions can be present in the mixtures. However, such mixtures of two different oxiranes can also be separated successfully by the process of the present invention using a dividing wall column having two side offtakes for liquid, as long as the boiling points are not too close together.

Figure 4:
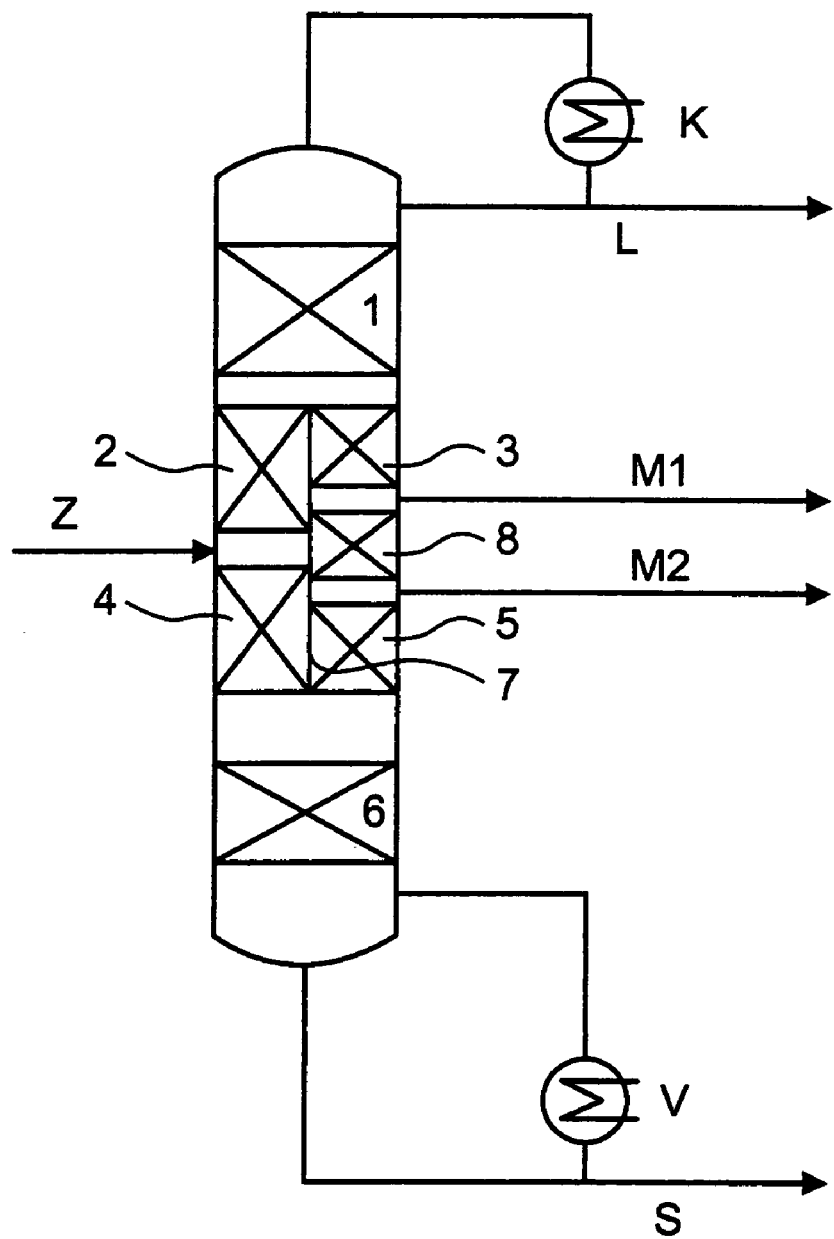
FIG. 4 shows a dividing wall column having two side offtakes.

A dividing wall column having two side offtakes is shown schematically in FIG. 4. Here, the lower-boiling oxirane is taken off at the upper side offtake M1 and the higher-boiling oxirane is taken off at the lower side offtake M2. In this arrangement, the region of thermal coupling 8 preferably has from five to fifty percent, more preferably from fifteen to thirty percent, of the total number of theoretical plates in the column.

In a preferred embodiment of the oxirane synthesis, hydrogen peroxide is used as hydroperoxide and the organic compound is brought into contact with a heterogeneous catalyst during the reaction. Further preference is then given to propylene oxide being used as organic compound and the oxirane being propylene oxide. Thus, in a particularly preferred embodiment, the process of the present invention comprises the continuously operated intermediate separation of the propylene oxide formed in the coproduct-free propylene oxide synthesis from the remaining components of the product stream using a dividing wall column.

The invention also provides an apparatus for carrying out a continuously operated process for the purification by distillation of the oxirane formed in the oxirane synthesis by reaction of a hydroperoxide with an organic compound, which comprises at least one reactor for preparing the oxirane and at least one dividing wall column for purifying the oxirane by distillation.

In a preferred embodiment of an apparatus for carrying out a continuously operated process for the purification by distillation of the oxirane formed in the oxirane synthesis by reaction of a hydroperoxide with an organic compound, the apparatus for preparing the oxirane comprises at least one isothermal reactor and one adiabatic reactor for carrying out the steps (i) and (iii) and a separation apparatus for the step (ii) and a dividing wall column for purifying the oxirane by distillation.

The dividing wall column can comprise at least two thermally coupled columns.

The invention is illustrated by the following example.

EXAMPLE

Propylene oxide was prepared from propylene and hydrogen peroxide by the multistage process described in WO 00/07965. The crude propylene oxide obtained had the following approximate composition:
about 0.2% by weight of low-boiling components comprising the key components methyl formate and acetaldehyde,
about 99.0% by weight of propylene oxide,
about 0.8% by weight of high-boiling components comprising the key components methanol, water and 1,2-propylene glycol.

The objective of the distillation was to obtain a pure propylene oxide having a purity of at least 99.99%, i.e. having a total content of key components of less than 0.01% by weight. For this purpose, the mixture was distilled in a dividing wall column having from 45 to 100 theoretical plates at a pressure at the top of 3 bar and a temperature of 62° C. The heating power of the bottom vaporizer of the dividing wall column was set so that the total concentration of these components in the product taken off at the side was less than 0.01% by weight.

The required energy content of the distillation, which was calculated from the vaporizer power and the amount of material passed through the column per hour, was used as a measure of the effectiveness of the separation. As column configurations, the arrangements shown in the table were selected:

| Column configuration | Energy requirements/(kg of propylene oxide/h) [kW/(kg propylene oxide/h)] | Energy saving [%] |
| --- | --- | --- |
| Conventional column with side offtake | 1.95 | — |
| Two conventional columns connected in series | 1.74 | 10.8 |
| Dividing wall column | 1.45 | 25.6 |

It is clear that the dividing wall configuration had a considerable energy advantage over the two conventional distillation arrangements. In addition, the thermal stress on the highly reactive and thermally labile product was lower, since significantly lower reflux ratios were necessary for the separation compared to the conventional column with side offtake. As a result, the residence time of the product in the column including vaporizer was lower. Compared to the series arrangement, the product was thermally stressed only once in a vaporizer.

LIST OF REFERENCE NUMERALS FOR FIGS. 1, 2, 3 AND 4

| | |
| --- | --- |
| 1 | Combined region of the inflow and offtake part of the dividing wall column |
| 2 | Enrichment section of the inflow part |
| 3 | Stripping section of the offtake part |
| 4 | Stripping section of the inflow part |
| 5 | Enrichment section of the offtake part |
| 6 | Combined region of the inflow and offtake part |
| 7 | Dividing wall |
| 8 | Region of thermal coupling |
| Z | Feed |
| L | Low boilers |
| M | Side offtake for intermediate boilers |
| M1 | Side offtake for lower-boiling oxirane |
| M2 | Side offtake for higher-boiling oxirane |
| S | High boilers |
| K | Condenser |
| V | Vaporizer |
| d | Vapor |
| f | Liquid |

Horizontal and diagonal or indicated diagonal lines in the columns symbolize packing made up of random packing elements or ordered packing which may be present in the column.

We claim:

1. A continuously operated process for the purification by distilling a crude oxirane formed in an oxirane synthesis by reacting a hydroperoxide with an organic compound, the process comprising separating the crude oxirane by distilling the crude oxirane into low-, intermediate- and high-boiling fractions in a dividing wall column, and taking off purified oxirane as the intermediate boiler fraction at a side offtake, wherein the dividing wall column has from 30 to 120 theoretical plates, wherein the distillation is carried out at a temperature from 35 to 110° C. and a pressure from 1 to 10 bar, with the temperature being measured at the side offtake and the pressure being measured at the top of the column, and wherein the dividing wall column is configured as thermally coupled columns.

2. The process as claimed in claim 1, wherein no impurity is present in the purified oxirane in a concentration of above 0.1% by weight, or the sum of all impurities is not greater than 0.1% by weight.

3. The process as claimed in claim 1, wherein the crude oxirane is prepared by a process comprising at least the steps (i) to (iii):

(i) reacting the hydroperoxide with the organic compound to give a product mixture comprising the reacted organic compound and unreacted hydroperoxide, (ii) separating the unreacted hydroperoxide from the mixture resulting from step (i), and (iii) reacting the hydroperoxide which has been separated off in step (ii) with the organic compound, wherein an isothermal fixed-bed reactor is used in step (i), an adiabatic fixed-bed reactor is used in step (iii) and a separation apparatus is used in step (ii), and wherein the hydroperoxide is hydrogen peroxide, wherein the organic compound is propylene, wherein the reaction occurs over a heterogeneous catalyst to form propylene oxide as oxirane, and wherein the heterogeneous catalyst is a titanium containing silicalite TS-1.

4. The process as claimed in claim 3, wherein no impurity is present in the purified oxirane in a concentration of above 0.1% by weight, or the sum of all impurities is not greater than 0.1% by weight.

* * * * *